US00PP32074P3

(12) United States Plant Patent
Austin

(10) Patent No.: US PP32,074 P3
(45) Date of Patent: Aug. 18, 2020

(54) ***ROSA HYBRIDA* SHRUB PLANT NAMED 'AUSCARTOON'**

(50) Latin Name: *Rosa hybrida*
Varietal Denomination: AUScartoon

(71) Applicant: David Austin Roses Ltd., Albrighton, Wolverhampton (GB)

(72) Inventor: David J. C. Austin, Albrighton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 16/350,907

(22) Filed: Jan. 30, 2019

(65) Prior Publication Data

US 2020/0100411 P1 Mar. 26, 2020

(30) Foreign Application Priority Data

Sep. 21, 2018 (GB) ..... PBR 5/2139

(51) Int. Cl.
*A01H 5/02* (2018.01)
*A01H 6/74* (2018.01)

(52) U.S. Cl.
USPC ..... Plt./104
CPC ..... *A01H 6/749* (2018.05)

(58) Field of Classification Search
USPC ..... Plt./104
CPC ..... A01H 6/749; A01H 5/02
See application file for complete search history.

*Primary Examiner* — Keith O. Robinson
(74) *Attorney, Agent, or Firm* — KPPB LLP

(57) ABSTRACT

A variety of rose plant of the shrub class, named 'AUScartoon'. The 'AUScartoon' is a variety of a rose shrub having a healthy, branching growth with many large single yellow blooms held in open sprays that is free flowering with a light musk scent.

1 Drawing Sheet

CROSS-REFERENCE TO RELATED APPLICATION

The present application claims priority to UK Varietal Plant Patent 5/2139, filed Sep. 21, 2018.

Classification: The present invention relates to a new *Rosa hybrida* shrub of the market class 'English Rose'.

Variety denomination: The new plant has the varietal denomination 'AUScartoon'.

ORIGIN OF INVENTION

This invention relates to a new and distinct variety of shrub rose plant named 'AUScartoon', which was originated from the cross-pollination of the two 'unnamed' and unpatented seedlings of *Rosa hybrida.*

BACKGROUND OF THE INVENTION

The primary objective of this breeding was to produce a healthy rose shrub having a branching growth with many large single yellow blooms held in open sprays that is free flowering with a light musk scent.

SUMMARY OF THE INVENTION

Among the features which distinguish the new variety from others presently available and commercial rose cultivars known to the inventor is the following combination of characteristics: open sprays of large, single yellow blooms with a light musk scent, good disease resistance and a rounded and branching growth.

Asexual reproduction of the new variety by budding as performed in Albrighton, Britain shows that the foregoing and other distinguishing characteristics come true to form and are established and transmitted through succeeding asexual propagations. 'AUScartoon' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUScartoon' are two unnamed seedlings. The new rose may be distinguished from its maternal parent, by the following combination of characteristics: the maternal parent has an apricot colored bloom with more petals, a semi-double bloom, and larger growth than 'AUScartoon'. The new rose may be distinguished from its paternal parent, by the following combination of characteristics: the paternal parent has white, single blooms and a more upright growth than 'AUScartoon'.

COMPARISON WITH THE CLOSEST COMMERCIALLY AVAILABLE CULTIVAR

The closest commercially available cultivar to the new variety is the unpatented *R. Xanthina* Var. *Spontanea* 'Canary Bird', which also has a yellow single bloom, although the flower is smaller. Specifically, the flowers of 'Canary Bird are 5 cm across, whereas the flowers of 'AUScartoon' are 9 cm in diameter. In addition, the foliage of 'Canary Bird' is matt, gray-green, and fern-like, whereas the foliage of 'AUScartoon' is glossy, dark green and large.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUScartoon' specimens were made at the nursery in Albrighton, Wolverhampton, United Kingdom. The following description is of 5 year-old rose plants of the new variety grown in a garden environment in Albrighton, Britain in the month of June. Phenotypic expression may vary with environmental, cultural and climatic conditions, as well as differences in conditions of light and soil.

Flower characteristics:

*Blooming habit.*—Recurrent. The number of blooms per plant during the growing season is profuse, but there are too many to count.

*Bud.*—Size: About 2.8 cm long and 1.3 cm in diameter when the petals start to unfurl. Form: The bud form is elogated pointed ovoid. Color: When sepals first divide, the bud color is RHS 13B (yellow group). When half blown, the upper sides of the petals are RHS 12A (yellow group), and the lower sides of the petals RHS 13B (yellow group). Calyx: Shape: opens to a star shape, with the sepals folding back against the stems. Length: 2.9 cm. Diameter: 1.2 cm. Sepals: Arrangement: Regularly arranged. Color: Upper Surface: RHS 194B (grayed-green group). Lower Surface: RHS 145A (yellow-green group). Length: 2.9 cm. Width: 7 mm. Shape: Lanceolate. Surface texture: Upper Surface: Downy. Lower Surface: Smooth. Number: There are 3 normally appendaged sepals, and 2 unappendaged sepals with glandular edges. Sepal Extensions: Are strong. Receptacles: Color: RHS 146A (yellow-green group). Shape: Apple. Size: Small, about 1 cm long× 0.6 cm wide. Surface: Smooth. Peduncle: Length: Short, averaging about 5.5 cm. Surface: Smooth. Color: RHS 146C (yellow-green group). Strength: Normal.

*Blooms.*—Size: Large, average open diameter is about 9 cm. Borne: Several together approximately 8-10 blooms, the inflorescence having a rounded shape. Stems: Strength: Normal, average length is about 40 cm. Diameter: 5 mm. Form: When first open, bloom is cupped. Permanence of bloom: flattens. Flower Type: Single.

*Petalage.*—Number of petals under normal conditions: 5. Color: The upper sides of the petals are RHS 10C (yellow group). The reverse sides of the petals are RHS 10D (yellow group). The base of the petals has a yellow spot RHS 9A (yellow group) approximately 5 mm, although no discernible yellow spot is present due to the yellow color of the petal. Variegations: None. Discoloration: The general tonality at the end of the first day is RHS 10C (yellow group), and at the end of the third day is RHS 10D (yellow group). Fragrance: Slight. Character of fragrance: Musk.

*Petals.*—Texture: Satiny. Size: Width: 3.8 cm. Length: 4.5 cm. Surface: Smooth. Shape: Obovate. Margin: Notched with weak reflexing and weak undulation. Apex Shape: Rounded. Base Shape: Obtuse. Form: Very slightly incurved. Arrangement: Regular. Petaloids: Number: Almost none with some blooms having one petaloid. Color: RHS 10A (yellow group). Length: 2 cm. Width: 2 cm. Shape: Deformed petal. Margin: Irregular. Persistence: Petals drop off cleanly before drying. Lastingness: On the plant: Short about 3-4 days. As a cut flower: not tested.

*Reproductive parts.*—Stamens: Number: approximately 80. Length: 7 mm & 14 mm (in equal measure). Anthers: Length: 1.5 mm. Color: RHS 17A (yellow-orange group). Arrangement: Regular around styles. Filaments: Color: RHS 17A (yellow-orange group). Length: approximately 5.5-6 mm & 11-13 mm (in equal measure). Pollen: Color: RHS 22A (yellow-orange group). Amount: Scarce. Pistils: Number: Approximately 15. Length: 4 mm. Styles: Color: RHS 60B (red-purple group)+RHS 163B (grayed-orange group). Length: 7 mm. Stigmas: Color: RHS 22A (yellow-orange group). Length: approximately 7 mm. Hips: NONE Observed.

Plant characteristics:

*Plant form.*—Shrub.

*Plant growth.*—Vigorous.

*Age to maturity.*—2 years.

*Mature plant.*—Height: 1 m 40 cm. Width: 1 m 40 cm.

*Rootstock.*—*Rosa dumetorum* 'Laxa' for the observed plants.

*Foliage.*—Number: Leaflets on normal mid-stem leaves is: 5 (some 7 and some 3) (including terminal leaflet). Size: Large, about 18 cm long×13 cm wide. Quantity: Normal. Number of leaves per flowering stem is: 10. Color: New foliage: Upper side: RHS 146B (yellow-green group). Lower side: RHS 146C (yellow-green group). Old foliage: Upper side: RHS 137A (green group). Lower side: RHS 146B (yellow-green group).

*Leaflets.*—Size: About 6.3 cm long×3.4 cm wide. Shape: Pointed oval. Base Shape: Rounded. Apex Shape: Acuminate. Texture: Leathery. Glossiness: Strong. Edge: Serrated. Serrations: Single. Petiole: Color: RHS 138A (green group) upperside, with RHS 146A (yellow-green) underside. Length: 4.2 cm. Width: 1.5 mm. Surface Texture: Glandular. Petiole Rachis: Color: RHS 138A (green group). Underside: with prickles. Stipules: Length: 2.7 cm, glandular. Color: RHS 146C (yellow-green group). Auricle: Shape: Lanceolate. Length: 6 mm. Width: 1 mm. Color: RHS 146C (yellow-green group). Vein Color: Color: RHS 137A (green group). Venation Pattern: Reticulate.

*Wood.*—New Wood: Color: RHS 178B (grayed-red group). Bark: Smooth. Old Wood: Color: RHS 146B (yellow-green group). Bark: Smooth.

*Branching habit.*—Number: 14. Dimensions: Length: 60 cm. Diameter: 1 cm.

*Stems.*—Mature Stem: Length: 80 cm. Diameter: 1 cm. Internode Distance: 11 cm. The above measurements are all variable, depending on growing conditions in a season. Stem Pubescence Present: No.

*Prickles.*—Quantity: On main canes from base: Ordinary. Number per stem length: 12 per 20 cm. On laterals from main canes: Ordinary. Number per stem length: 12 per 20 cm mainly in bottom third of stem. Form: Deep concave. Length: 6 mm. Color When Young: RHS 199B (grayed-brown group). Color When Mature: RHS 199B (grayed-brown group).

*Small prickles.*—Quantity: Main stalk: None.

*Disease resistance.*—Powdery Mildew. (*Podosphaera pannosa*): Resistant. Downy Mildew. (*Peronospora* species): Resistant. Blackspot. (*Diplocarpon rosae*): Resistant. Rust. (*Phragmidium tuberculatum*): Resistant.

*Pest resistance.*—Not tested.

*Winter hardiness.*—Not tested.

*Growing conditions.*—Normal garden conditions.

What is claimed is:

1. A new and distinct variety of rose plant of the shrub class, substantially as herein shown and described.

* * * * *

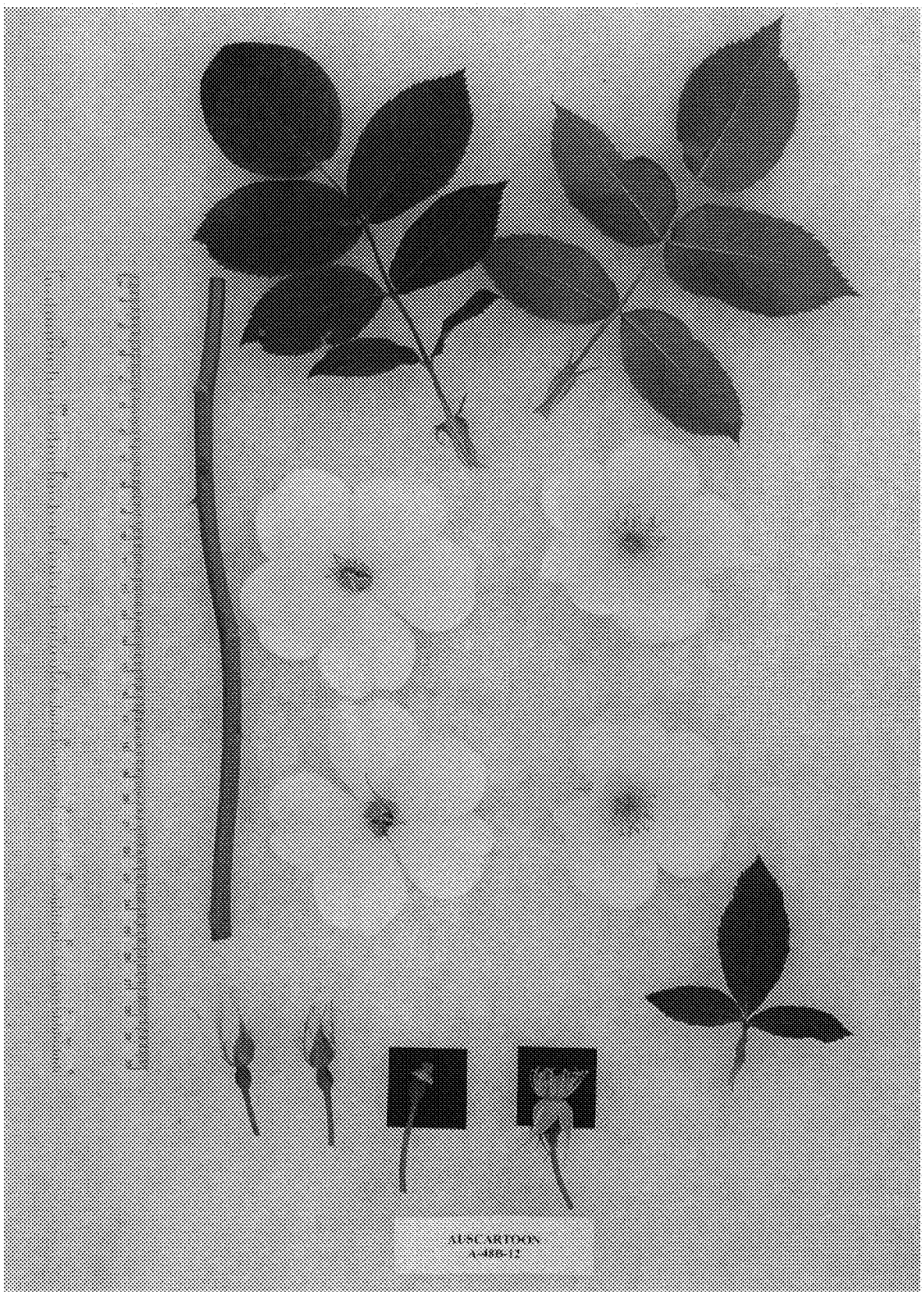
SESCARTOON
A-488-12